US012605509B1

(12) United States Patent
Alshehri et al.

(10) Patent No.: US 12,605,509 B1
(45) Date of Patent: Apr. 21, 2026

(54) ENHANCED DUAL BARREL SYRINGE ENCLOSURE WITH ROTATIONAL DETACHMENT SYSTEM FOR SIMULTANEOUS IRRIGATION AND ASPIRATION IN ENDODONTIC PROCEDURES

(71) Applicant: KING SAUD UNIVERSITY, Riyadh (SA)

(72) Inventors: Mohammed Abdullah Alshehri, Riyadh (SA); Omar Mohammed Alshehri, Riyadh (SA); Ibraheem Rshood Alqwizany, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/342,985

(22) Filed: Sep. 29, 2025

Related U.S. Application Data

(62) Division of application No. 19/249,657, filed on Jun. 25, 2025.

(51) Int. Cl.
A61M 5/31 (2006.01)
A61M 5/315 (2006.01)

(52) U.S. Cl.
CPC ...... A61M 5/3129 (2013.01); A61M 5/31511 (2013.01)

(58) Field of Classification Search
CPC .. A61M 5/19; A61M 5/2448; A61M 5/16827; A61M 5/3129; A61M 5/31511; A61M 5/14216; A61M 5/1422; A61M 5/1424; A61M 5/1408; A61M 1/67; A61M 1/815; A61M 1/81; A61M 1/774; A61M 3/0233; A61M 39/10; A61M 2205/106
See application file for complete search history.

(56) References Cited

U.S. PATENT DOCUMENTS

| | | | | |
|---|---|---|---|---|
| 4,902,281 | A | * | 2/1990 | Avoy ........................ B05B 1/26 222/137 |
| 5,378,233 | A | * | 1/1995 | Haber ................. A61M 5/2066 D24/114 |
| 5,919,182 | A | * | 7/1999 | Avallone ............. A61M 5/3202 141/27 |
| 6,827,701 | B2 | | 12/2004 | McMahon et al. |
| 7,018,382 | B2 | | 3/2006 | Merboth et al. |

(Continued)

*Primary Examiner* — Michael J Tsai
*Assistant Examiner* — Justin L Zamory
(74) *Attorney, Agent, or Firm* — Nath, Goldberg & Meyer; Joshua B. Goldberg

(57) ABSTRACT

A dual barrel syringe assembly includes first and second cover components, a first barrel and a first plunger in fluid communication with one another, a second barrel and a second plunger in fluid communication with one another, a tip piece connectable to the first and/or second cover components, a trigger rotatably coupled to at least one of the first and second cover components, and a mechanism connecting the trigger to the first and second plungers, the mechanism being configured to move the first and second plungers in an opposing synchronous manner in response to a rotational movement of the trigger. A method of using the dual barrel syringe assembly includes inserting first and second needles of the tip piece in a root canal of a patient and squeezing the trigger to release a sterilizing fluid in the root canal.

13 Claims, 7 Drawing Sheets

(56) References Cited

U.S. PATENT DOCUMENTS

| | | | |
|---|---|---|---|
| 7,674,247 B2 | 3/2010 | Fojtik | |
| 8,672,193 B2 | 3/2014 | Vukic et al. | |
| 10,058,656 B2 | 8/2018 | Fumiyama et al. | |
| 10,207,057 B2 | 2/2019 | Fotjik | |
| 12,053,342 B1 | 8/2024 | Alshehri et al. | |
| 2008/0154209 A1* | 6/2008 | Fojtik .................... | A61M 5/19 |
| | | | 604/191 |

* cited by examiner

ENHANCED DUAL BARREL SYRINGE ENCLOSURE WITH ROTATIONAL DETACHMENT SYSTEM FOR SIMULTANEOUS IRRIGATION AND ASPIRATION IN ENDODONTIC PROCEDURES

CROSS-REFERENCE TO RELATED APPLICATION

This application is a divisional of U.S. patent application Ser. No. 19/249,657, filed on Jun. 25, 2025, the entire contents of which are incorporated herein by reference.

TECHNICAL FIELD

The present disclosure relates to a dual barrel syringe assembly, and more particularly, to a dual barrel syringe assembly usable in endodontic procedures and a method of using the same.

DISCUSSION OF THE RELATED ART

Dual barrel syringe assembles usable in endodontic procedures are generally known. The working principle of such devices, generally speaking, is to discharge a sterilizing fluid, often sodium hypochlorite, into a root canal of a tooth during a root canal procedure. The device then suctions the released sterilizing fluid from the root canal. However, known devices can be impractical for use. For example, these devices can be cumbersome, can release too much sterilizing fluid into a root canal at once and can cause operator hand fatigue, among other things.

SUMMARY

The present disclosure relates to a dual barrel syringe assembly usable in endodontic procedures. The dual barrel syringe assembly of the present subject matter includes a housing with an interior chamber. The interior chamber stores the moving components of the assembly that cause the plungers of the two barrels to move when a trigger of the assembly is squeezed.

A front tip piece of the dual barrel syringe assembly, which includes a first needle configured to eject fluid out of a first barrel and a second needle configured to suction the ejected fluid into a second barrel, is removably couplable to the housing, providing access to the two barrels when needed.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Figure 1:
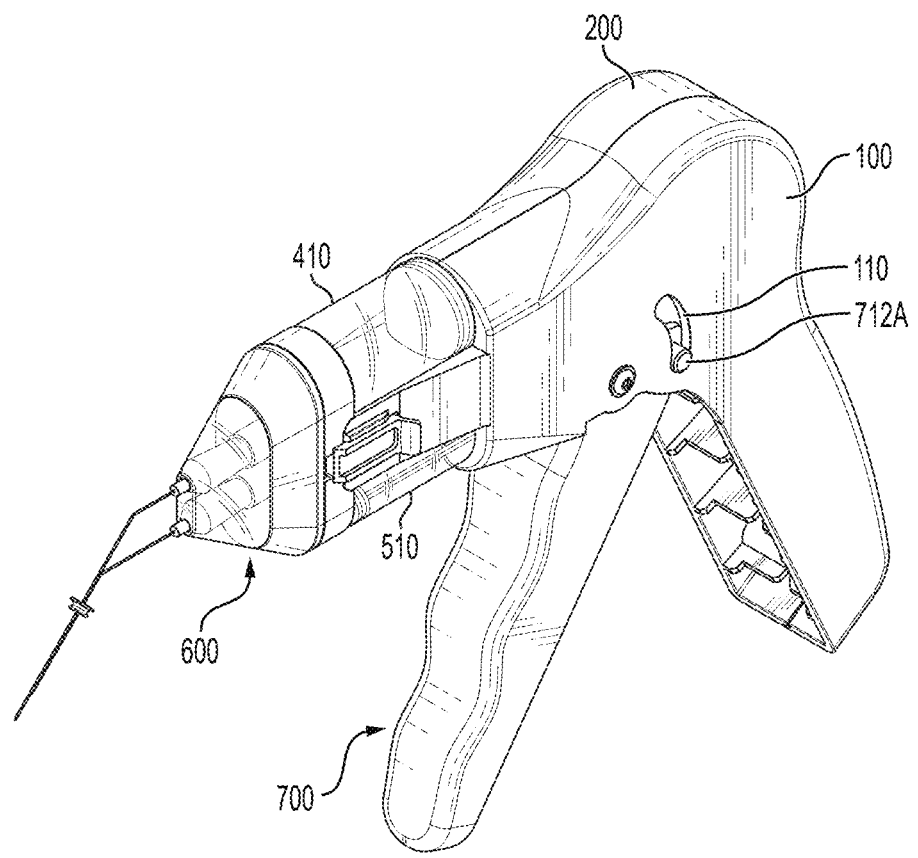
FIG. 1 is a perspective view illustrating a dual barrel syringe assembly according to the present subject matter.
Figure 2:
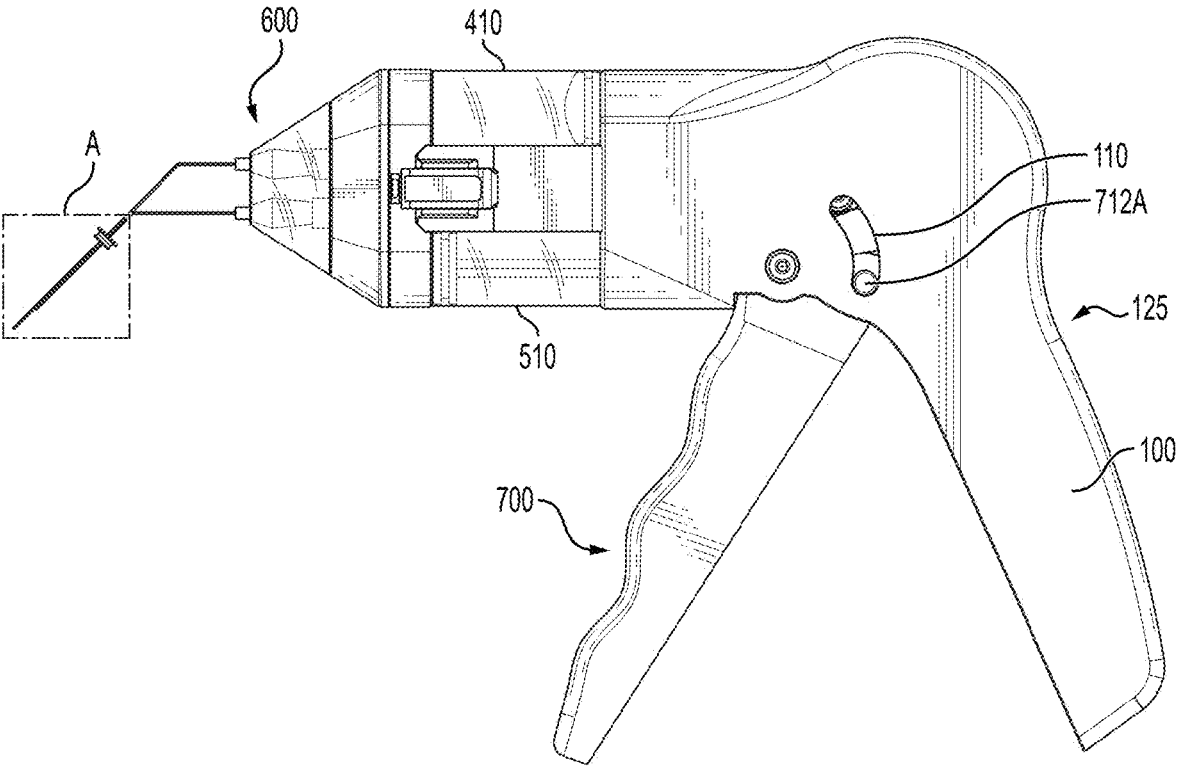
FIG. 2 is a side view illustrating the dual barrel syringe assembly of FIG. 1.

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Figure 5:
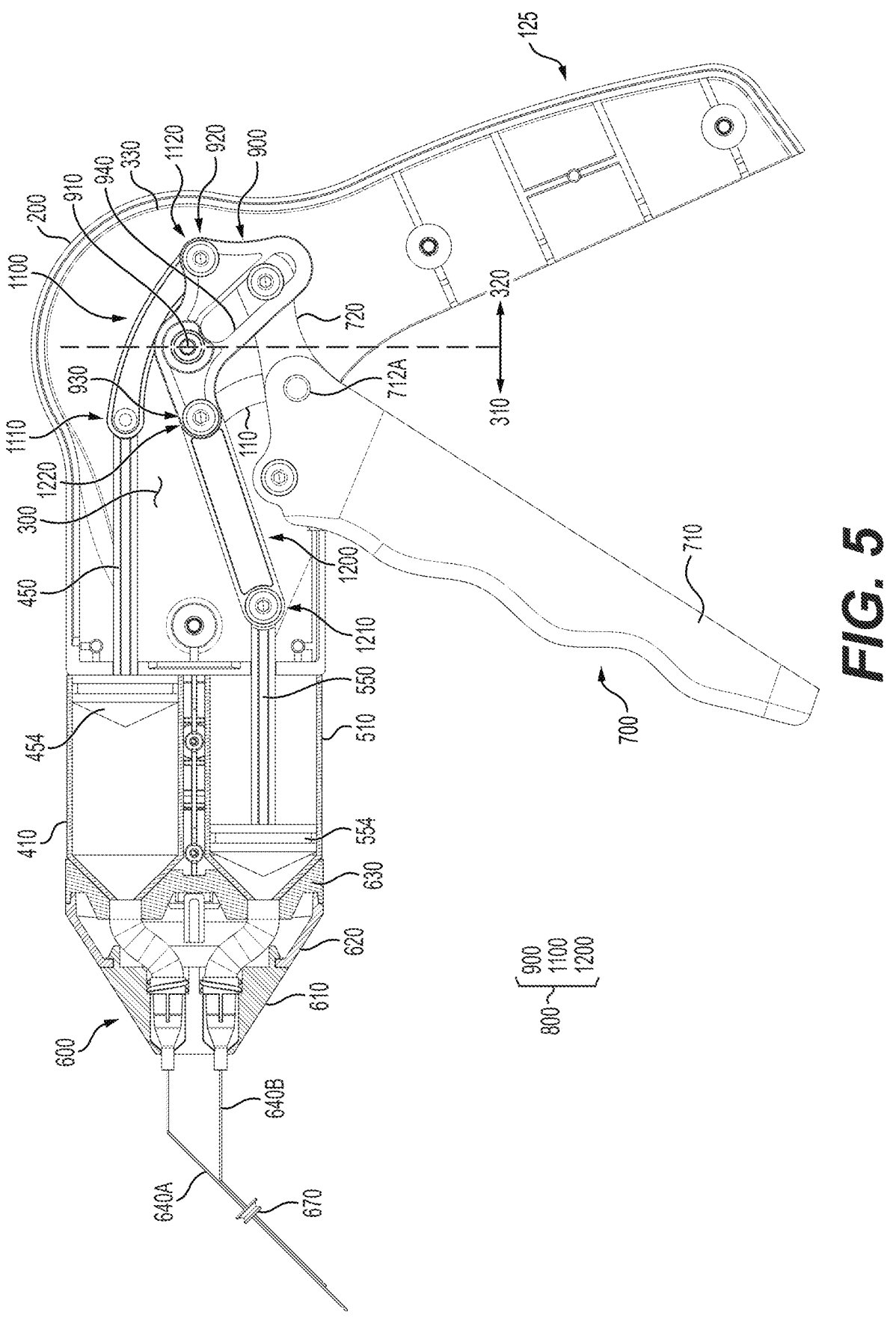
FIG. 5 is a side view illustrating the dual barrel syringe assembly of FIG. 1 in a first state, with a cover removed from a rear portion of the assembly and the front portion of the assembly shown in a cutaway view.
Figure 6:
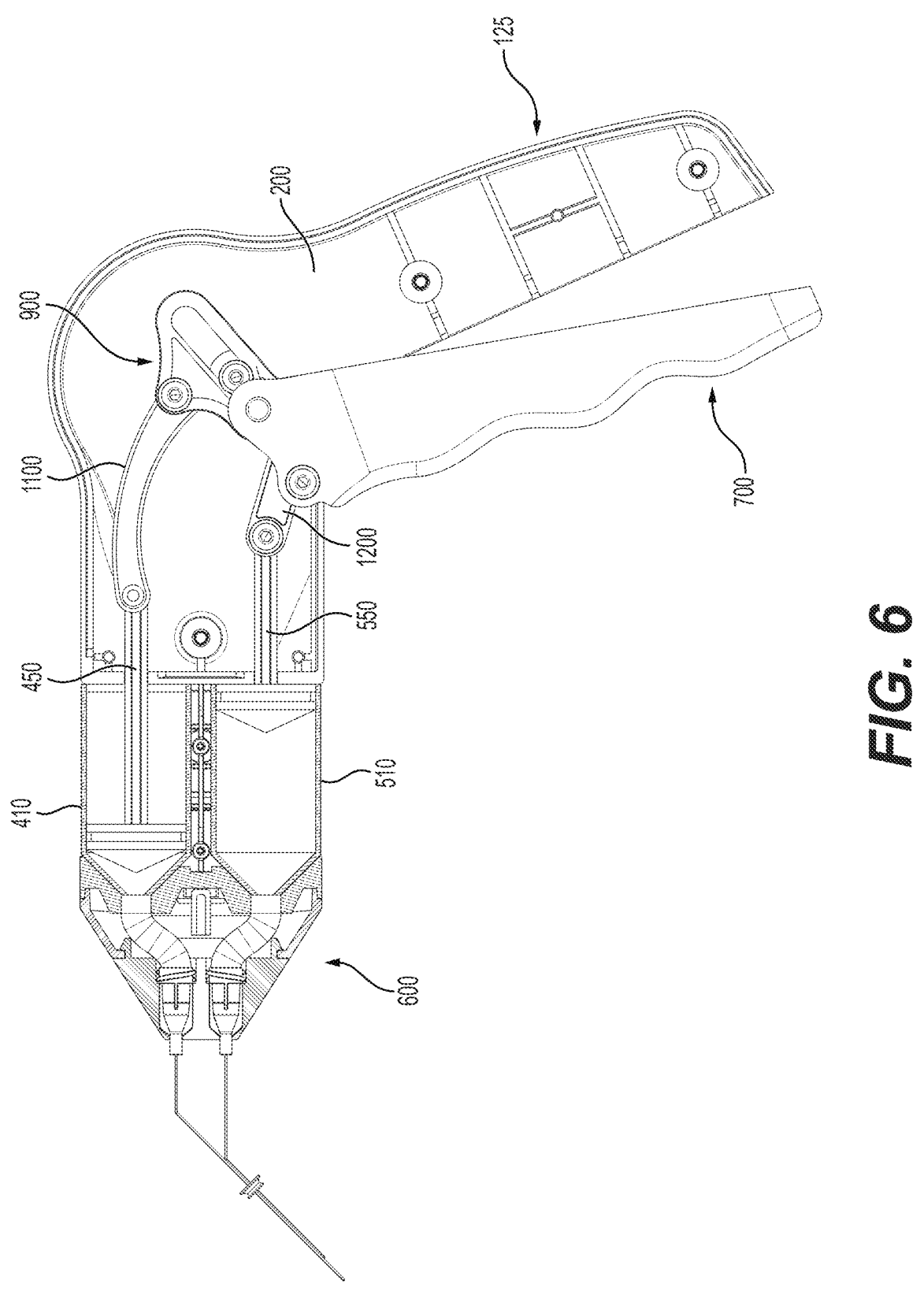
FIG. 6 is a side view illustrating the dual barrel syringe assembly of FIG. 1 in a second state, with the cover removed from the rear portion of the assembly and the front portion of the assembly shown in a cutaway view.

Referring to FIGS. 1-7, a dual barrel syringe assembly includes:

a first cover component 100 (see FIG. 3) and a second cover component 200, the first and second cover components 100, 200 defining a portion of an exterior of the dual barrel syringe assembly and an interior chamber 300 (see FIG. 5) of the dual barrel syringe assembly;

a first barrel 410 and a first plunger 450 in fluid communication with the first barrel 410 (see at least FIGS. 5-6), the first plunger 450 being movable between a retracted state relative to the first barrel 410 (as shown in FIG. 5), and an extended state relative to the first barrel (as shown in FIG. 6), the first plunger 410 extending in the interior chamber 300 of the dual barrel syringe assembly when positioned in the retracted state thereof;

a second barrel 510 and a second plunger 550 in fluid communication with the second barrel 510, the second plunger 550 being movable between a retracted state relative to the second barrel 510 (as illustrated in FIG. 6), and an extended state relative to the second barrel 510 (as illustrated in FIG. 5), the second plunger 550 extending in the interior chamber 300 of the dual barrel syringe assembly when positioned in the retracted state thereof;

a tip piece 600 (see at least FIG. 1) connectable to at least one of the first and second cover components 100, 200, the tip piece 600 being configured to selectively affix the first and second barrels 410, 510 to the at least one of the first and cover components 100, 200 when the tip piece 600 is connected to the at least one of the first and second cover components 100, 200, the tip piece 600 fluidly connecting the first and second barrels 410, 510 to an outside of the dual barrel syringe assembly;

a trigger 700 rotatably coupled to at least one of the first and second cover components 100, 200; and a mechanism 800 (see FIG. 5) connecting the trigger 700 to the first and second plungers 450, 550, the mechanism 800 being configured to move the first and second plungers 450, 550 in an opposing synchronous manner in response to a rotational movement of the trigger 700 (i.e., when the trigger 700 is rotated relative to the first and/or second cover components 100, 200).

The opposing synchronous manner, as illustrated with reference to the state of the first and second plungers 450,

550 in FIGS. 5 and 6, means that when the first plunger 450 is moved forward (e.g., from its retracted state in FIG. 5 to its extended state in FIG. 6), the second plunger 550 is moved backward (e.g., from its extended state in FIG. 5 to its retracted state in FIG. 6), and vice-versa.

Referring to FIG. 5, the mechanism 800 includes:

a central structure 900 having a body rotatably connected to at least one of the first and second cover components 100, 200;

a first arm 1100 rotatably connected to the first plunger 450 and rotatably connected to the central structure 900; and a second arm 1200 rotatably connected to the second plunger 550 and rotatably connected to the central structure 900. As illustrated in FIG. 5, the first and second arms 1100, 1200 may be rotatably connected to the central structure 900 at different locations (or different regions) of the central structure 900.

As illustrated in FIG. 5, the body of the central structure 900 may include an elongated through opening 940 spaced apart from the different locations of the central structure 900 where the first and second arms 1100, 1200 are rotatably connected to the central structure 900.

Referring to FIG. 5, the body of the central structure 900 of the mechanism 800 includes:

a first region 910 rotatably connecting the central structure 900 with at least one of the first and second cover components 100, 200;

a second region 920 spaced from the first region 910 of the body of the central structure 900; and a third region 930 spaced from the first region 910 of the body of the central structure 900, with the second and third regions 920, 930 of the body of the central structure 900 being spaced apart from one another.

Figure 3:
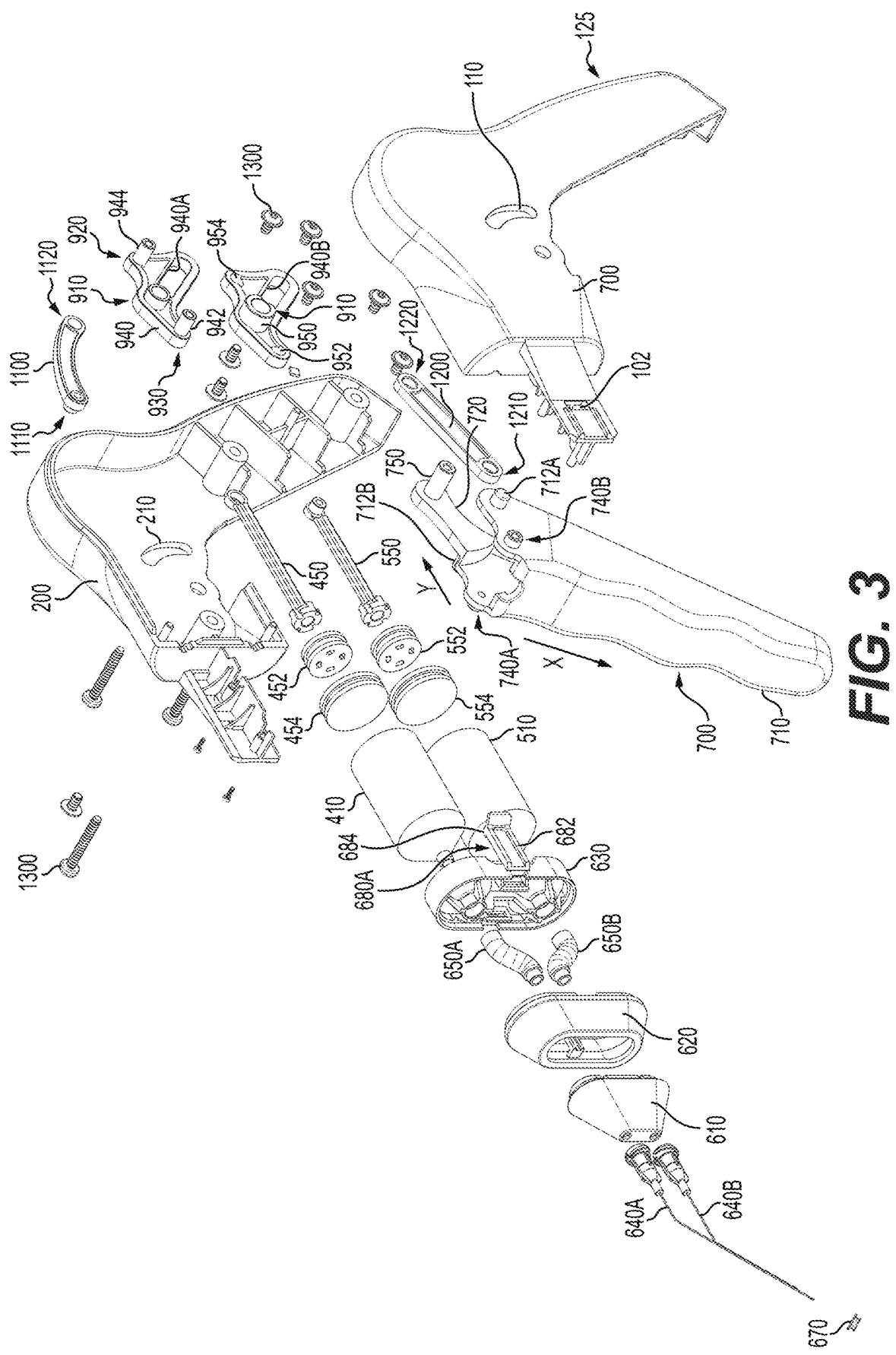
FIG. 3 is an exploded perspective view illustrating the dual barrel syringe assembly of FIG. 1.
Figure 4:
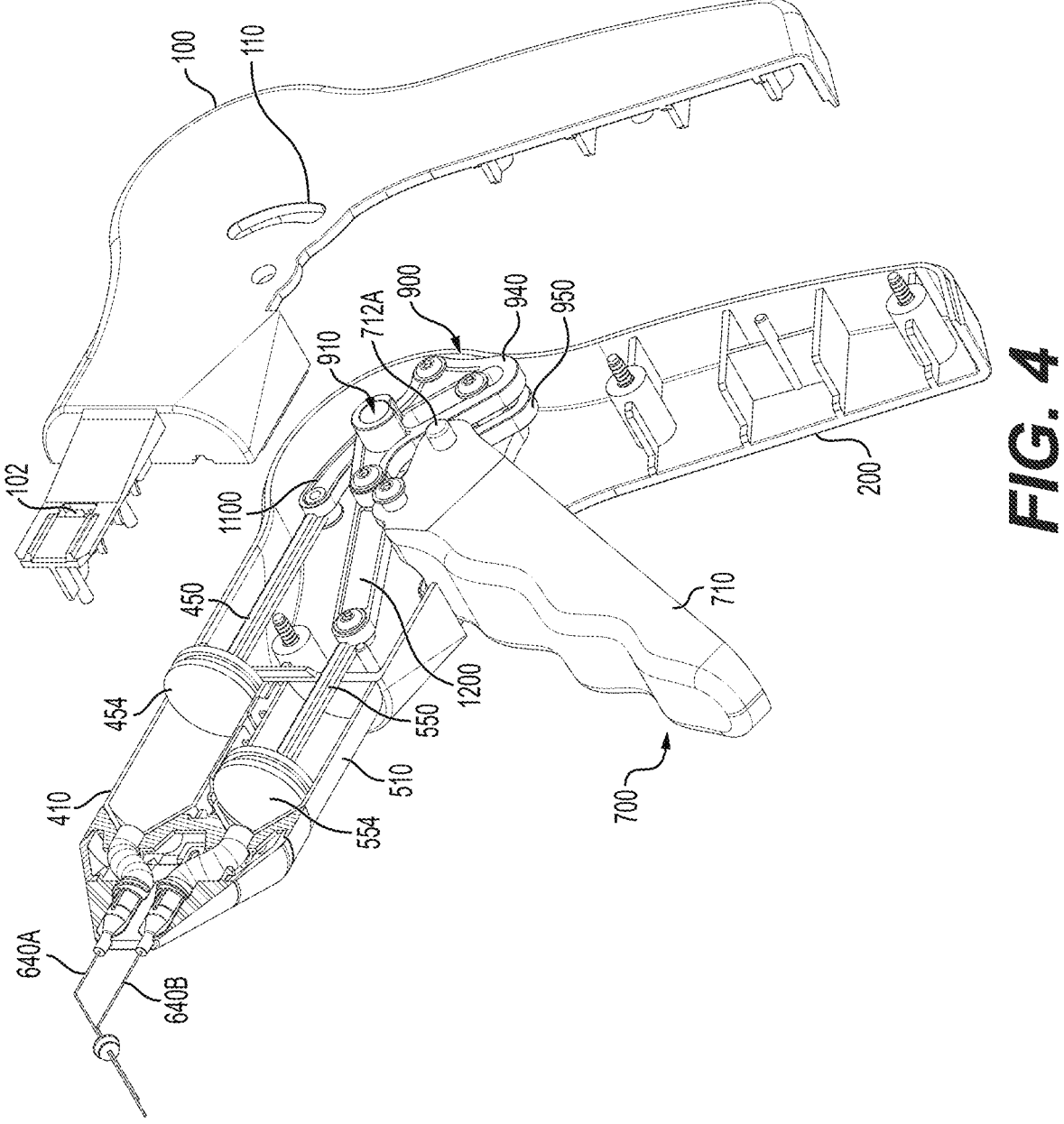
FIG. 4 is a composite view, illustrating the dual barrel syringe assembly of FIG. 1 in a partially exploded state with a cutaway of a front portion of the dual barrel syringe assembly.

As illustrated in FIGS. 3-5, the first region 910 of the central structure may be disposed between the second and third regions 920, 930 of the central structure.

The elongated through opening 940 is spaced apart from the second and third regions 920, 930 of the body of the central structure 900.

The first arm 1100 has a certain length. A first region 1110 of the first arm 1100 (e.g., a first end region of the firm arm 1100) is rotatably connected to the first plunger 450, and a second region 1120 of the first arm 1100 (e.g., a second end region of the firm arm 1100) is rotatably connected to the second region 920 of the body of the central structure 900.

The second arm 1200 has a certain length. A first region 1210 of the second arm 1200 (e.g., a first end region of the second arm 1200) is rotatably connected to the second plunger 550, and a second region 1220 of the second arm 1200 (e.g., a second end region of the second arm 1200) is rotatably connected to the third region 930 of the body of the central structure 900.

As illustrated in FIGS. 3-6, the rotatable connections between the first and second plungers 450, 550, the first and second arms 1100, 1200 and the central structure 900 may be, merely as an example and without limitation, hinged connections. Said hinged connections may be formed by utilizing a bar that extends though a through hole at the regions of the first and second plungers 450, 550, the first and second arms 1100, 1200 and the central structure 900 described in this specification. The "bar" may be, merely as an example, a fastener 1300 (e.g., a screw), as more clearly illustrated in FIG. 3.

As more clearly illustrated in FIG. 3, the body of the central structure 900 may include a first body component 940 and a second body component 950. The first and second body components 940, 950 may be similar in shape and size to one another, and may be selectively coupleable to one another.

Referring to FIG. 3, a first bar 942 and a second bar 944 may protrude from the first body component 940. The second body component 950 may include a first through hole 952 and a second throng hole 954.

Referring to FIG. 3, the first bar 942 may extend through a through hole in the second region 1220 of the second arm 1200 and through the first through hole 952 of the second body component 950. The second bar 944 may extend through a through hole in the second region 1120 of the first arm 1100 and through the second through hole 954 of the second body component 950.

As illustrated in FIG. 3, a first elongated through opening 940A in the first body component 940 and a second elongated through opening 940B in the second body component 950 together may define the elongated through opening 940.

Referring to FIGS. 1-6, the trigger 700 is rotatable between an extended state and a retracted state. The trigger 700 is illustrated in the extended state in FIGS. 1-5, and in the retracted state in FIG. 6.

When the trigger 700 is in the extended state thereof (see FIG. 5), the first plunger 450 is in the retracted state and the second plunger is in the extended state (see FIG. 5). When the trigger 700 is in the retracted state (see FIG. 6), the first plunger 450 is in the extended state and the second plunger 550 is in the retracted state (see FIG. 6).

Referring to FIG. 3-6, the trigger 700 includes:

a first lever portion 710 extending in a first direction X (see FIG. 3) from a region 740A, 740B (or hinge region 740A, 740B, see FIG. 3) of the trigger 700, where the trigger 700 rotatably connects to at least one of the first and second cover components 100, 200; and a second lever portion 720 extending in a second direction Y (see FIG. 3) from the region 740A, 740B of the trigger 700.

The second lever portion 720 includes a protrusion 750 extending in the elongated through opening 940 of the body of the central structure 900.

The protrusion 750 is slidably coupled to the elongated through opening 940 such that a rotation of the trigger 700 relative to at least one of the first and second cover components 100 (about the hinge region 740A, 740B of the trigger 700), 200 is configured to rotate the second lever portion 720, causing the protrusion 750 to be slid along a length of the elongated through opening 940, in turn, causing the central structure 900 to be rotated relative to at least one of the first and second cover components 100, 200, thereby causing the first and second arms 1100, 1200 to move the first and second plungers in an opposing synchronous manner.

Referring to FIG. 5, the interior chamber 300 includes:

a front portion 310, the front portion 310 of the interior chamber 300 extending between the first and second barrels 410, 510 and a location where the central structure 900 is rotatably connected to at least one of the first and second cover components 100, 200 (e.g., the first region 910 of the central structure 900), and a rear portion 320, the rear portion 320 of the interior chamber 300 extending between the location where the central structure 900 is rotatably connected to at least one of the first and second cover components 100, 200 (e.g., the first region 910) and a rear 330 of the first and second cover components 100, 200, opposite to the first and second barrels 410, 510.

Referring to FIG. 5, when the trigger 700 is in an extended state thereof, with the first plunger 450 in the retracted state and the second plunger 550 in the extended state, the first arm 1100 extends partially in the front portion 310 of the interior chamber 300 and partially in the rear portion 320 of the interior chamber 300.

Referring to FIG. 5, when the trigger 700 is in the extended state thereof, the second arm 1200 extends entirely in the front portion 310 of the interior chamber 300.

As illustrated in FIGS. 3-6, the first arm 1100 may be curved and the second arm 1200 may be straight.

The elongated through opening 940 of the body of the central structure 900 may delimit an amount of rotation of the trigger 700 by virtue of the elongated through opening 940 restricting a movement of the protrusion 750 of the second lever portion 720 along its length (i.e., along the length of the elongated through opening 940).

Alternatively, or in addition, a cutout in the first and/or second cover components 100, 200 may be used to restrict the amount of rotation of the trigger 700. More specifically, with reference to FIG. 3, at least one of the first cover component 100 and the second cover component 200 includes a curved through opening (or cutout) 110, 210. For example, the first cover component 110 may include the curved through opening 110, and the second cover component may include the curved through opening 210.

The first lever portion 710 of the trigger 700 may include a pair of second protrusions 712A, 712B. The second protrusion 712A may extend in the curved through opening 110, and/or the second protrusion 712B may extend in the curved through opening 210.

Any one (or both) of the curved through openings 110, 210 may delimit an amount of rotation of the trigger 700 by virtue of the curved through opening 110 and/or 210 restricting a movement of any one of the pair of second protrusions 712A, 712B of the first lever portion 710 along its length (i.e., along a length of the curved through opening 110 and/or 210).

The first barrel 410 can be filled with a fluid that an endodontist may wish to discharge inside of a root canal of a patient, for example, for sterilization purposes or maintaining a hygienic environment inside of the root canal while the endodontist works on the root canal. The fluid may be, for example, sodium hypochlorite. The first barrel 410 may be sized to include an amount of fluid that is sufficient to last for the entire root canal procedure (e.g., for the root canal procedure of one tooth). Merely as an example, the first barrel 410 may be sized to accommodate about 10 ml of fluid inside when the first plunger is in the retracted state, as shown in FIG. 5.

In a non-limiting example, a rotation of the trigger between the extended and retracted states thereof is delimited to about 55 degrees (relative to the first and/or second cover component 100, 200). This amount of rotational movement of the trigger 700 offers a comfortable experience for an endodontist in squeezing or pulling the trigger 700 (e.g., accounting for the size of a hand of numerous humans) while discharging the fluid content of the first barrel 410 between the retracted and extended states of the first plunger 450.

In use, when the dual barrel syringe assembly is in the state illustrated in FIG. 5, the first barrel 410 would preferably be substantially full of fluid and the second barrel 510 would preferably be substantially empty of fluid.

The second barrel 510 may be shaped and sized similarly (or substantially the same) as the first barrel. The second barrel 510 is configured to store the fluid discharged from the first barrel 410 via a suction created when the trigger 700 is squeezed toward a handle 125 of the dual barrel syringe assembly (e.g., when the trigger 700 is rotated toward its retracted state shown in FIG. 6).

As illustrated in FIG. 3, the first plunger 450 may include a first flange 452 and a first seal 454. The second plunger 550 may include a second flange 552 and a second seal 554. The first and second seals 454, 554 may be made of, for example, silicone.

The first and second barrels 410, 510 may be made of an elastomeric material (e.g., a plastic material). The elastomeric material may be, for example, translucent in order to indicate the location of the seals 454, 554 in the first and second barrels 410, 510. However, the first and second barrels 410, 510 may also be made of glass, an opaque elastomeric material and/or of a metal.

Referring to FIG. 3, the tip piece 600 may include first to third body components 610, 620, 630 (which may be selectively connectable to one another), a first needle 640A configured to discharge fluid from the barrel 410 through a first conduit 650A, and a second needle 640B configured to suction fluid from a root canal (e.g., the fluid discharged from the first needle 640A) such that the suctioned fluid can flow into the second barrel 510 via a second conduit 650B.

Figure 7:
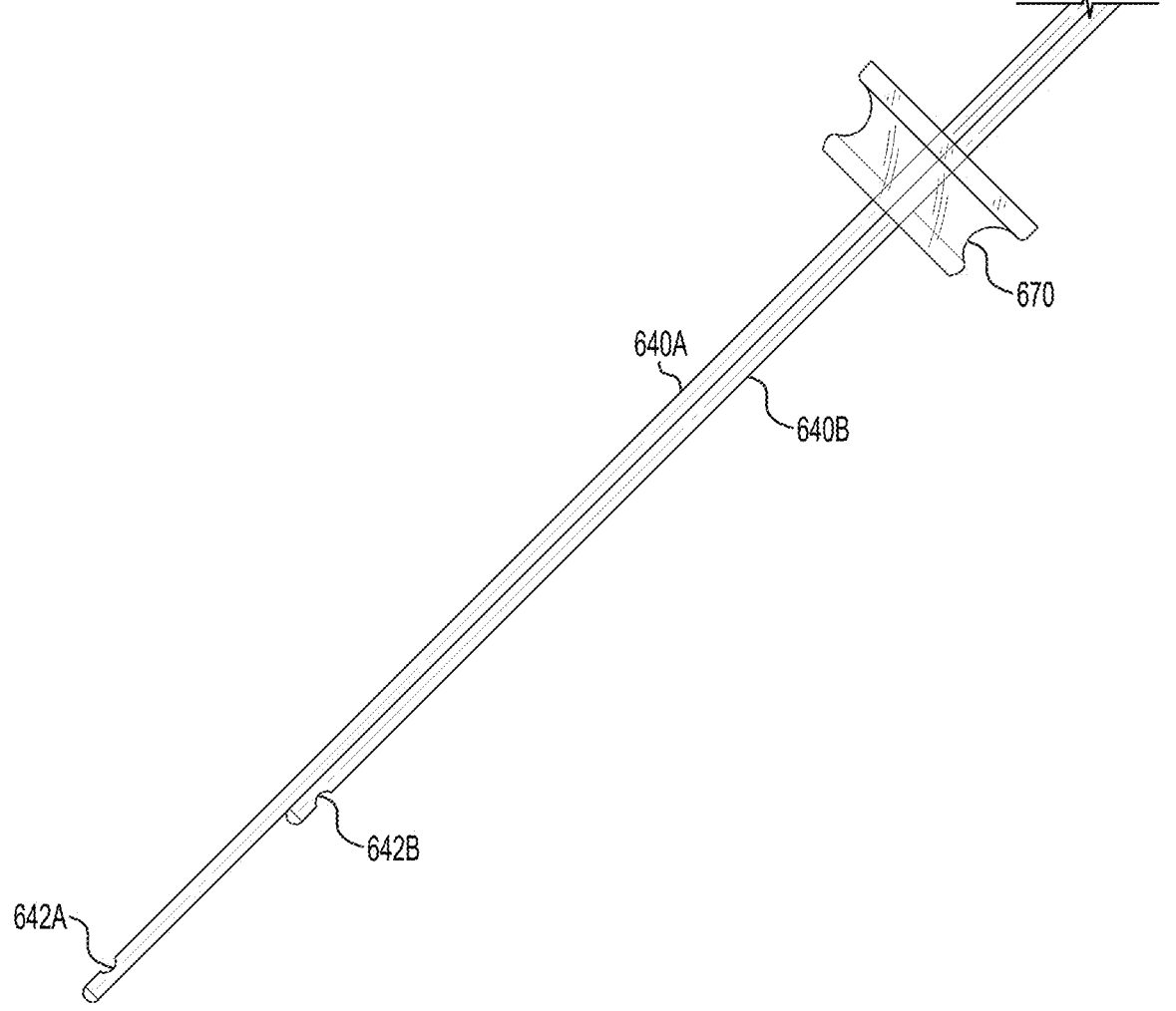
FIG. 7 is a magnified view illustrating a portion A of FIG. 2.

As illustrated in FIG. 7, the first needle 640A includes an opening 642A. The opening 642A may be spaced apart from a distal end of the first needle 640A. The second needle 640B includes an opening 642B. The opening 642B may be spaced apart from a distal end of the second needle 640B.

The first and second needles 640A, 640B may be made of a metal (e.g., stainless steel).

The first and second conduits 650A and 650B may be made of a flexible elastomeric material (e.g., rubber, silicone, etc.,), or of an elastomeric material having a greater rigidity than rubber (e.g., polycarbonate, etc.).

The fasteners 1300 may be made of a metal (e.g., steel, etc.). All other components of the dual barrel syringe assembly, the composition of which is not specifically described in this specification, may be made of an elastomeric material (e.g., a plastic material, including, without limitation, polycarbonate, polyethylene, etc.,) and/or a metal.

The tip piece 600 may also include holding component 670 configured to configured to hold (or keep) the first and second needles 640A, 640B adjacent or close to one another.

Moreover, the tip piece 600 may include a first locking member 680A (see FIG. 3). The first locking member 680A (which may be connected to the third body component 630) may include an elongated bar 682 and a protrusion 684 extending from the elongated bar 682. The elongated bar 682 and the protrusion 684 of the first locking member 680A are configured to overlap the exterior of the dual barrel syringe assembly (e.g., the exterior of the first cover component 100) when the tip piece 600 is connected to at least one of the first and second cover components 100, 200.

As illustrated in FIG. 3, the first cover component 100 may include a recess 102. The recess 102 is configured to accommodate the protrusion 684 of the first locking member 680A to maintain the tip piece 600 and the at least one of the first and second cover components 100, 200 selectively connected to one another. A user can pull the cantilevered end of the elongated bar 682 to dislodge the protrusion 684 from the recess 102, thus enabling the tip piece 600 to be disconnected from the first and/or second cover components 100, 200.

In addition, the tip piece 600 may also include a second locking member opposite to the first locking member 680A. The second locking member may have a similar structure to that of the first locking member 680A, but in a mirror configuration relative to the first locking member 680A. The second cover component 200 may have a second recess to accommodate a protrusion of the second locking member therein. This way, the tip piece 600 can be selectively secured to the first and second cover component 100, 200 from opposing sides thereof.

The construction of a dual barrel syringe assembly as described in this specification can be manufactured for a reasonable price and can be convenient to use on dental patients. The housing of the moving components of the dual barrel syringe assembly in the interior chamber 300 is advantageous because it protects the moving components from the damage that can result from contact with foreign objects, and because it presents the dual barrel syringe assembly in a convenient package.

For example, the housing of the moving components of the dual barrel syringe assembly in the interior chamber 300 prevents the moving components from inadvertently coming into contact with a patient's face while an endodontist performs a root canal procedure, as can occur with know dual barrel syringe assemblies.

In addition, the removable nature of the first and second barrels 410, 510, in conjunction with the selective connection between the tip piece 600 and the first and second cover components 100, 200, provides ease of access to the first and second barrels 410, 510 (for refilling purposes, for example) while being able to securely connect the first and second barrels 410, 510 to the first and second cover components 100, 200.

The shape and/or size of the trigger 700 and the handle 125, in conjunction with the about 52 degree rotatability of the trigger 700 relative to the handle 125 (and relative to the first and second cover components 100, 200), enables discharging with precision an effective amount of fluid inside of a root canal while reducing operator hand fatigue over an extended period of time (since root canal procedures can last a relatively long time).

A method of using a dual barrel syringe assembly includes obtaining a dual barrel syringe assembly as described in this specification with reference to FIGS. 1-7. In the obtained dual barrel syringe assembly, the first barrel 410 is filled at least partially with a fluid configured to sterilize or clean a root canal of a patient.

The method includes inserting the first needle 640A and the second needle 640B of the tip piece 600 of the obtained dual barrel syringe assembly in a root canal of a patient.

The method then includes squeezing the trigger 700 such that the first needle 640A discharges a quantity of the fluid in the root canal and, via the opposing synchronous movement of the first and second plungers 450, 550, the second plunger 550 creating suction via the second needle 640B such that at least a portion of the discharged quantity of fluid can be conveyed into the second barrel 510.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. A method of using a dual barrel syringe assembly, the method comprising:

obtaining a dual barrel syringe assembly, the dual barrel syringe assembly including:

a first cover component and a second cover component defining a portion of an exterior of the dual barrel syringe assembly and an interior chamber of the dual barrel syringe assembly;

a first barrel and a first plunger in fluid communication with the first barrel, the first plunger being movable between a retracted state, relative to the first barrel, and an extended state, relative to the first barrel, the first plunger extending in the interior chamber of the dual barrel syringe assembly when positioned in the retracted state thereof;

a second barrel and a second plunger in fluid communication with the second barrel, the second plunger being movable between a retracted state, relative to the second barrel, and an extended state, relative to the second barrel, the second plunger extending in the interior chamber of the dual barrel syringe assembly when positioned in the retracted state thereof;

a tip piece connectable to at least one of the first and second cover components, the tip piece being configured to selectively affix the first and second barrels to the at least one of the first and cover components when said tip piece is connected to the at least one of the first and second cover components, said tip piece fluidly connecting the first and second barrels to an outside of the dual barrel syringe assembly;

a trigger rotatably coupled to at least one of the first and second cover components; and a mechanism connecting the trigger to the first and second plungers, the mechanism being configured to move the first and second plungers in an opposing synchronous manner in response to a rotational movement of the trigger relative to at least one of the first and second cover components, wherein the first barrel is filled at least partially with a fluid configured to sterilize or clean a root canal of a patient;

inserting a first needle and a second needle of the tip piece of the dual barrel syringe assembly in a root canal of a patient; and squeezing the trigger such that the first needle discharges a quantity of the fluid in the root canal and, via the opposing synchronous movement of the first and second plungers, the second plunger creating suction via the second needle such that at least a portion of the discharged quantity of fluid can be conveyed into the second barrel, wherein the mechanism includes:

a central structure having a body rotatably connected to at least one of the first and second cover components;

a first arm rotatably connected to the first plunger and rotatably connected to the central structure; and a second arm rotatably connected to the second plunger and rotatably connected to the central structure, the first and second arms being rotatably connected to the central structure at different locations of the central structure, wherein the body of the central structure includes an elongated through opening spaced apart from said different locations of the central structure where the first and second arms rotatably connect to the central structure, and wherein the trigger includes:

a first lever portion extending in a first direction from a region of the trigger where the trigger rotatably connects to the at least one of the first and second cover components; and a second lever portion extending in a second direction from the region of the trigger where the trigger rotatably connects to the at least one of the first and second cover components, wherein said second lever portion includes a protrusion extending in the elongated through opening of the body of the central structure, the protrusion being slidably coupled to the elongated through opening such that a rotation of the trigger relative to at least one of the first and second cover components is configured to rotate the second lever portion, causing the protrusion to be slid along a length of the elongated through opening, in turn, causing the central structure to be rotated relative to at least one of the first and second cover components, thereby causing the first and second arms to move the first and second plungers in the opposing synchronous manner.

2. The method of claim 1, wherein the body of the central structure of the mechanism includes:

a first region thereof rotatably connecting the central structure with at least one of the first and second cover components;

a second region thereof spaced from said first region of the body of the central structure; and a third region thereof spaced from said first region of the body of the central structure, the second and third regions of the body of the central structure being spaced apart from one another, wherein the elongated through opening is spaced apart from the second and third regions of the body of the central structure.

3. The method of claim 2, wherein the first arm has a length with a first region of said first arm rotatably connected to the first plunger and a second region of said first arm rotatably connected to the second region of the body of the central structure; and wherein the second arm has a length with a first region of said second arm rotatably connected to the second plunger and a second region of said second arm rotatably connected to the third region of the body of the central structure.

4. The method of claim 2, wherein the first region of the central structure is disposed between the second and third regions of the central structure.

5. The method of claim 1, wherein the trigger is rotatable between an extended state and a retracted state, when the trigger is in the extended state thereof, the first plunger is in the retracted state and the second plunger is in the extended state thereof, and when the trigger is in the retracted state thereof, the first plunger is in the extended state thereof and the second plunger is in the retracted state thereof.

6. The method of claim 1, wherein a rotation of the trigger between the extended and retracted states thereof is delimited to about 55 degrees.

7. The method of claim 1, wherein the trigger is rotatable between an extended state and a retractable state, wherein the elongated through opening of the body of the central structure delimits an amount of rotation of the trigger by virtue of said elongated through opening restricting a movement of the protrusion of the second lever portion along the length thereof.

8. The method of claim 1, wherein the trigger is rotatable between an extended state and a retractable state, wherein at least one of the first cover component and the second cover component includes a curved through opening, wherein the first lever portion includes a second protrusion, said second protrusion of the first lever portion extending in the curved through opening of the at least one of the first cover component and the second cover component, and wherein the curved through opening delimits an amount of rotation of the trigger by virtue of the curved through opening restricting a movement of the second protrusion of the first lever portion along a length thereof.

9. The method of claim 1, wherein the interior chamber includes:

a front portion thereof, the front portion of the interior chamber extending between the first and second barrels and a location where the central structure is rotatably connected to at least one of the first and second cover components; and a rear portion thereof, the rear portion of the interior chamber extending between the location where the central structure is rotatably connected to at least one of the first and second cover components and a rear of the first and second cover components, opposite to the first and second barrels, wherein, when the trigger is in an extended state thereof, with the first plunger in the retracted state thereof and the second plunger in the extended state thereof, the first arm extends in the front portion of the interior chamber and in the rear portion of the interior chamber.

10. The method of claim 9, wherein the first arm is curved.

11. The method of claim 9, wherein, when the trigger is in the extended state thereof, the second arm extends entirely in the front portion of the interior chamber.

12. The method of claim 9, wherein the second arm is straight.

13. The method of claim 1, wherein the tip piece includes a locking member, said locking member including an elongated bar and a protrusion extending from the elongated bar, the elongated bar and the protrusion of the locking member being configured to overlap the exterior of the dual barrel syringe assembly when the tip piece is connected to at least one of the first and second cover components, and the first cover component includes a recess configured to accommodate therein the protrusion of the locking member to maintain the tip piece and the at least one of the first and second cover components selectively connected to one another.

\* \* \* \* \*